United States Patent [19]

Ricci

[11] Patent Number: 4,854,501

[45] Date of Patent: Aug. 8, 1989

[54] FRAGRANCE SACK

[76] Inventor: Fannie Ricci, 129 Trail East, Hendersonville, Tenn. 37075

[21] Appl. No.: 210,138

[22] Filed: Jun. 14, 1988

Related U.S. Application Data

[63] Continuation of Ser. No. 906,693, Sep. 11, 1986, abandoned, which is a continuation of Ser. No. 673,713, Nov. 21, 1984, abandoned.

[51] Int. Cl.$^4$ .............................................. A61L 9/12
[52] U.S. Cl. ........................................ 239/54; 239/55
[58] Field of Search ...................... 239/34, 36, 53–58, 239/60

[56] References Cited

U.S. PATENT DOCUMENTS

| | | | |
|---|---|---|---|
| 743,340 | 11/1903 | Simundt | 239/57 |
| 750,847 | 2/1904 | Groff | 239/57 |
| 774,902 | 11/1904 | Acheson | 239/57 |
| 893,740 | 7/1908 | Leeper | 239/57 |
| 1,029,105 | 6/1912 | Clarke | 239/54 |
| 2,218,037 | 10/1940 | Duers et al. | 239/57 |
| 2,529,578 | 11/1950 | Thompson | 239/55 |
| 3,129,888 | 4/1964 | O'Hagan | 239/55 |
| 3,947,971 | 4/1976 | Bauer | 239/60 |
| 4,345,716 | 8/1982 | Armstrong et al. | 239/56 |
| 4,465,232 | 8/1984 | Field | 239/60 |

*Primary Examiner*—Andres Kashnikow
*Assistant Examiner*—Michael J. Forman
*Attorney, Agent, or Firm*—John J. Byrne

[57] ABSTRACT

A fragrance sack for selectively scenting the surrounding area comprises an outer layer of cosmetically attractive material covering an upper surface and a lower surface, filler material contained within the outer layer, a replaceable scenting element anchored to the outer surface layer, and a receiving pocket formed in the seam between the meeting edges of the upper and lower surface of the outer layer. The scenting element carries the desired fragrance and is inserted into the receiving pocket to provide the fragrance sack with the desired odor. In addition, the scenting element may be removed from the pocket to be renewed with the same fragrance or replaced by a new scenting element having a different fragrance. In this manner, the fragrance sack may carry an acceptively strong odor for an extended period of time or may carry a variety of different odors.

1 Claim, 2 Drawing Sheets

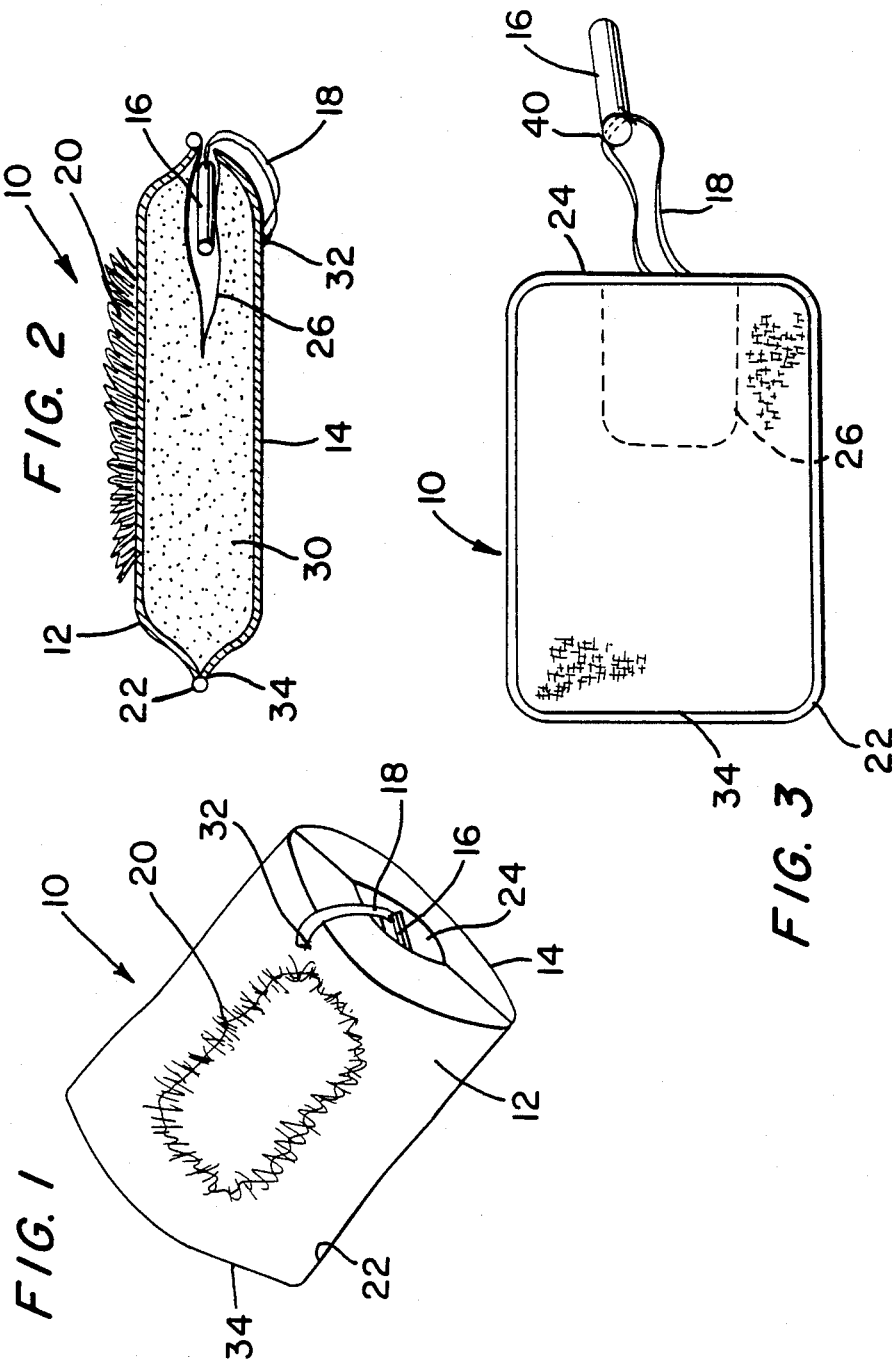

FRAGRANCE SACK

This application is a continuation, of application Ser. No. 006,693, filed Sept. 11, 1986 now abandoned which is a continuation, of application Ser. No. 673,713, filed Nov. 21, 1984 now abandoned.

BACKGROUND OF THE INVENTION

This invention relates to a fragrance sack having an attractive pillow-shaped case for disseminating agreeable odors such as perfumes, aromas, and fragrances. More particularly, this invention relates to a free formed and relatively simple and uncomplicated arrangement for providing scenting in a variety of applications.

The present invention provides a renewable, replaceable, scent element secured to the fragrance sack and positioned in a receiving pocket in the sack. Such features add a high degree of attractiveness to the sack as well as a personal selectivity in the fragrance originally utilized or in a replacement fragrance used in association with the sack. In particular, the inventive fragrance sack of the present invention provides an economical alternative to fragrance sacks of the prior art which utilize non-replaceable, non-renewable, scent packets permanently fabricated within the sack or which provide a relatively unattractive means for receiving a scent element.

Fragrance sacks carrying various perfumes and enlivening the olfactory senses have long been recognized as a means for supplementing and enhancing pleasant odors with additional agreeable odors. Accordingly, in the art and practice of scented sacks there are a variety of arrangements for adding a fragrance by the placement of a scent carrying packet within the sack. Typically, such arrangements utilize a package of scent carrying material such as rose petals or dried herbs which emit a characteristic smell.

A significant problem associated with a number of fragrance sacks constructed in accordance with the prior art is that the fragrance dissipates very rapidly. In fact, in some cases the sacks lose their fragrance almost entirely between manufacture and purchase, which results in either an unhappy customer or a lost sale. Another significant problem in sacks of the prior art is that the consumer is typically presented with fragrance sacks which have a scent package permanently sewn in. Thus, the discriminating decorator or taste-conscious shopper is left with a choice which is necessarily of a permanent nature. Moreover, the choice is often relatively limited in that every fragrance package may not be available in each decorator design.

A wide variety of constructions have been utilized in the prior art for providing fragrance sacks. Frequently, however, such sacks have featured a decorative cover for powdered scenting material and carried the scent producing material in an air permeable package. The package would then be pinned to clothing or placed in close proximity to that which a characteristic smell is to be imparted. Alternatively, the perfumed powder has been placed within perforated and wire lined lids of a can-type container, and in another construction a pad of lamb's wool wrapped in a piece of gauze and stitched into a strip of material for attachment to undergarments by a safety pin has been utilized wherein perfume is added to the pad.

Because articles of the type described above require either the replacement of the whole scenting structure or the careful freshening of a pad while it remains in place in a carrier, the range of usefulness of such articles is somewhat limited.

In sharp contrast, the subject invention is directed to a soft and flexible fragrance sack having a decorative design which provides the user with a refreshable scent element which may be removed for rescenting or replaced with a new element and which remains attached to the sack while residing in an open pocket.

Although a number of prior designs have provided for replacement or renewal of a fragrance, significant problems have been occasioned with such constructions. For example, one construction of a sachet has an extending ribbon end closure providing access to an unstuffed cavity which receives a charge of perfumed powder. This design, however, requires the unstuffing of the entire article to enfold a quantity of scented powder into a cotton mass to provide a fresh charge of powder. Similarly, another design uses an adhesive adornment to carry a scented pellet in an open pocket cut into the front face of a two layer stitched construction. However, this design provides no retaining means for the scenting element, and in addition, the scent saturated pellet resides on the backside of the decorative facing material thus suscepting the facing to straining.

Still another design of the prior art presents a frangible sealed capsule of perfume which is centrally located in a stuffed casing and which delivers its contents into the stuffing material to provide a fragrance arrangement. In this design, however, interior stuffing material is scented and throwaway is practiced.

These limitations of disassembly for replacement, replacing a powder charge, simple placement in an open pocket, and low protection of the carrier from stain or damage by the scent element are inherent in the above designs. Accordingly, while such devices, as previously noted, have achieved at least a degree of recognition in the area of fragrance enhancement, room for significant improvement remains.

The subject invention is directed toward a fragrance sack providing for retention of a scenting element in an open pocket not permitted in prior structures. Moreover, the present invention enables the user to combine the desired fragrance sack design with the desired fragrance, and to replace or renew the fragrance of the sack at any time.

The problems suggested in the preceding are not intended to be exhaustive, but rather are among many which may reduce the effectiveness and user satisfaction of prior fragrance sack devices. Other noteworthy problems may also exist; however, those presented above should be sufficient to demonstrate that fragrance enhancement particularly of the replaceable element type appearing in the prior art have not been altogether satisfactory.

OBJECTS OF THE INVENTION

It is, therefore, a general object of the invention to provide a novel free-formed decorative fragrance sack having an interior pocket for receiving a replaceable scent element which will obviate or minimize difficulties of the type previously described.

It is a specific object of the invention to provide a novel non-attachable fragrance sack for providing a means for scenting garments in a closet or dresser drawer.

It is a specific object of the invention to provide a novel self contained fragrance sack for providing means to scent bread or other baked goods stored in proximity to the sack.

It is another object of the invention to provide a novel fragrance sack having provision to carry replaceable scenting elements which may be advantageously employed in homes and residences during holiday seasons to give an appealing fragrance to the residential surroundings.

It is yet another object of the invention to provide a novel fragrance sack for carrying a replaceable scent element in an open pocket which can be placed in proximity to a heat source to disperse a desirable fragrance throughout a living area by the convective heat flow of the air.

It is a further object of the invention to provide a novel attractively adorned fragrance sack having a releasable, replaceable and retainable scent element retained in an open pocket in the sack.

It is yet a further object of the invention to provide a novel fragrance sack for placement in a boudoir or lady's vanity area or in a bathroom alongside fragranced soaps and which has a renewable scent element that may be custom scented for advantageous blending with the prevailing fragrance character.

It is another object of the invention to provide a novel fragrance sack for scenting personal stationery by placement in a writing desk or drawer for storing writing supplies.

It is still another object of the invention to provide a novel free formed fragrance sack made into the desirable shapes of Christmas ornaments or other such ornaments for hanging on a Christmas tree; such a sack having replaceable scenting elements useable season after season.

It is yet another object of the invention to provide a novel fragrance sack having means to remove laundry odors from a clothes hamper and to maintain towels and linen items in pleasant smelling condition.

It is yet another object of the invention to provide a novel fragrance sack having a protective feature for the scent element so as not to expose it unnecessarily to outer air and waste or easily exhaust the perfume.

It is yet another object of the invention to provide a novel fragrance sack construction which prevents outer surfaces of the sack from becoming soiled should the scent element be over saturated during a refreshing procedure.

It is yet another object of the invention to provide a novel fragrance sack which may advantageously be employed in hotel suites and country inns to provide custom fragrances.

It is yet another object of the invention to provide a novel fragrance sack which may advantageously be used by airlines and coach operations to mask distracting odors and to promote a fragrance theme such as tropical scents for Hawaii tours.

It is yet another object of the invention to provide a novel fragrance sack having a scent element which can be conveniently carried by a person to a cosmetic counter and a sample of a fragrance under consideration may be applied to the cartridge for transport back to a bedroom or boudoir for a decision on whether such a fragrance is to be purchased for continued use.

It is yet another object of the invention to provide a novel fragrance sack having an embellished external appearance thus making an attractive accessory.

It is yet another object of the invention to provide a novel fragrance sack for placement on a gentlemen's bachelor chest among toiletries with a masculine scent such as sandalwood.

BRIEF SUMMARY OF THE PREFERRED EMBODIMENT OF THE INVENTION

A preferred embodiment of the invention which is intended to accomplish at least some of the foregoing objects comprises a pillow-shaped case stuffed with filler material and having an interiorly projecting pocket or cavity for receiving a scent saturated rod of cotton which is releasably connectable to a ribbon fastened to an exterior surface of the pillow. The interiorly projecting pocket is positioned at a seam where the top and bottom halves of the sack case are joined and remains open to the outside surface of the pillow or sack. The interiorly positioned faces of the pocket lie spaced apart from contact with the inner surfaces of the top and bottom halves of the sack case and filler material occupies the space therebetween. A decorative arrangement of lace and ribbon may adorn the exterior surface of the filled sack or pillow.

THE DRAWINGS

Other objects and advantages of the present invention will become apparent from the following detailed description of a preferred embodiment thereof taken in conjunction with the accompanying drawings wherein:

FIG. 1 is an axonometric view of a fragrance sack of the type to advantageously utilize the subject invention.

FIG. 2 is a cross sectional view taken longitudinally through the fragrance sack at the interiorly extending pocket.

FIG. 3 is a plan view of a fragrance sack according to the invention showing the scent element retained on a ribbon.

DETAILED DESCRIPTION

Context of the Invention

Before presenting a detailed description of the subject fragrance sack it may be worthwhile to briefly outline the context of the instant invention. In this connection FIGS. 4 and 5 exemplify some of the uses of a fragrance sack of the present invention which may advantageously employ a replaceable scent element.

As mentioned previously, the fragrance sack of the instant invention has numerous other applications including those in the personal items arena, in household scenting and in commercial settings.

Figure 4:
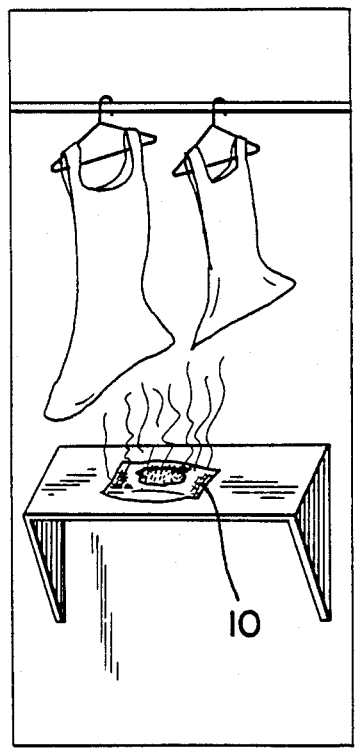
FIGS. 4 and 5 are diagrammatic views showing by way of an example the placement of a fragrance sack in a recommended setting.
Figure 5:
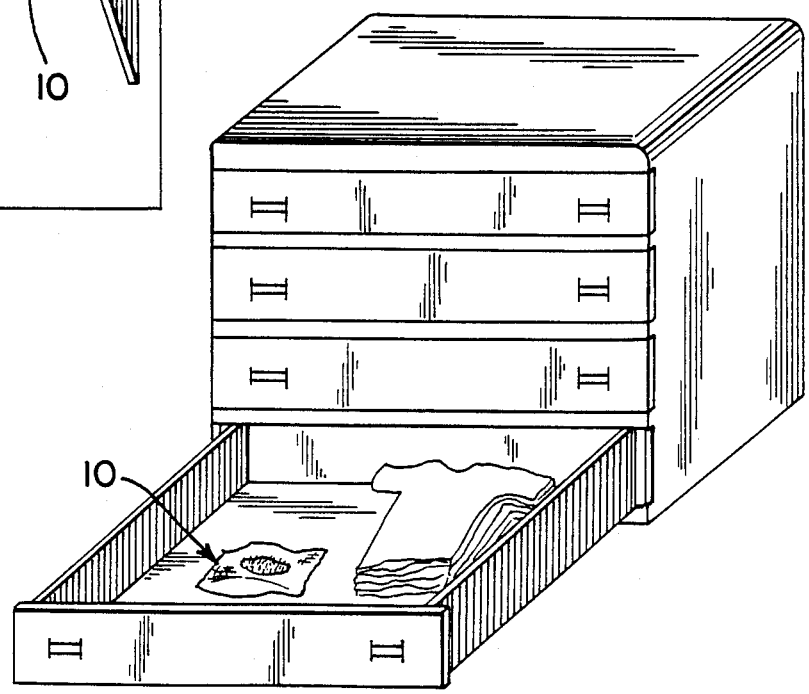

The present invention advantageously includes a detachable scent element which may be carried in an open pocket in the sack to allow pleasant odors to permeate the surroundings. In use, the fragrance sack may be placed on a shelf as shown in FIG. 4 to add a pleasant scent to items of clothing stored in a closet, or in a drawer as depicted in FIG. 5. Other areas where advantageous placement is contemplated include: (1) in a bathroom near scented soaps, (2) on a lady's vanity table, (3) in a gentleman's dressing area, (4) near warm fresh baked goods to add a cinnamon or other spice-like scent, (5) in and around holiday decorations to enhance the festive occasion with fragrances associated with the season, (6) near a source of convective heat in a residence, automobile or business to freshen and brighten the prevailing scents, and (7) in accommodations such as in hotels as well as in air and ground coach travel cabins.

Fragrance Sack

The construction of the subject inventive fragrance sack 10 is best shown in FIGS. 1-3. In this regard, a pillow-like case has a top half 12 and a bottom half 14 joined at a peripheral seam 34 and has a pocket opening 24 along one seamed edge. An interiorly extending pocket 26 resides interiorly and is positioned so as to be spaced apart from the lower surface of the top half 12 and the upper surface of the bottom half 14 by an intermediate mass of fill material 30. A decorative facing 20 of upstanding lacework adorns the upper surface of the top half 12, and a length of edge piping 22 extends around the periphery of the sack and adds an attractive and functional protective rib over the seam 34.

The outer covering of top half 12 and bottom half 14 is selected with a view toward an efficient transfer of desirable fragrance scents through the material and, depending on the intended use, may be any suitable material such as cotton, silk, nylon, wool or other woven or knitted fabric. A fragrance element 16 is positioned in the pocket 26 through the pocket opening 24 which opens along one of the edge seams 34 along the periphery of the sack. The element 16 is attached to the sack 10 at an anchor 32 by a length of ribbon 18 which is attached to the element by a releasable connection such as a hook or a pin, (not shown). In use, however, the fragrance element 16 is placed deep within the pocket 26 so that only the cosmetically attractive ribbon 18 is seen entering the pocket opening 24.

By use of the ribbon 18 acting as a connector, the pocket opening 24 is allowed to remain open and the ribbon 18 retains the scent element 16 even if by handling the element 16 become dislodged from the interior pocket 26. Such an arrangement advantageously allows superior diffusion of the scent because the pocket remains open, however, a slide fastener commonly referred to as a zipper or a button closure may be used if it is deemed desirable to close the pocket 26.

The filler material 30 is a stuffing of a suitable material such as loosely-associated unwoven fabric which may be partly felted. Desirably the fibers should be so associated that they tend to distend the case and to resiliently resist flattening to thus maintain an attractive overall contour. Such filler material may be man-made synthetic fibers or natural material from animals or plants such as cotton or may be a mixture thereof.

Fragrance or scenting element 16 is formed from an absorbent material such as balsam, cotton, fibrous paper or any other suitable absorbing material. Balsam wood is a particularly preferred scenting element due to its relatively long retention of fragrances. The rescenting element may be formed into a cylindrical shape, or other shapes such as a sphere or ring.

The scent impregnated element 16 acts as a conveyor and is saturated with a volatile fluid such as perfume, toilet water, man's cologne or other desirable fragrances. It is contemplated that essential oils be used to saturate the scenting element, that is, any of a class of volatile oils possessing the desirable odor characteristics. Usually these essential oils are carried in an alcohol solution. The scenting element 16 may be refreshed by removal from the pocket, while remaining attached to the ribbon connector, and saturating with additional oils. If a different fragrance is to be applied to the sack, the same scenting element can be used, however, preferably the scenting element is detached from the anchoring ribbon and discarded, the sack refreshed by dry cleaning or other means and a new scented element attaches to the ribbon and inserted.

It is also to be understood that the conveyor element 16 can additionally carry a scented powdered material if desired. In this manner, scents such as oil of cinnamon and oil of cloves or balsam may be advantageously applied to the scent element 16 depending upon the anticipated use of the fragrance sack, or other scents can be applied according to the desires of the user.

A releasable connector device 40 is used to secure the ribbon 18 to the scented element. Such connector devices provide a releasable connection allowing disposal of the scent element after a period of use, and among those suggested for use is a "swiss latch" type of single use plastic connector which provides an eye for inserting a free end into and pulling teeth on the length of the connector past a restriction in the eye to form a secure connection which may cut with scissors to release.

The particular construction of the present invention provides the protective layers of the pocket 26 and the intermediate filler material 30 between the scented element and the inner side of the decorative facing 20 top half 12 of the sack to prevent staining of the embellished external decoration. The decorative facing 20 may be a piece of embroidery, an applique, or lace-type cover mounted on one face or half of the sack.

Having described in detail a preferred embodiment of the invention and before proceeding with the claim portion of the specification, it may be useful to briefly set forth some of the major advantages of the invention.

SUMMARY OF THE MAJOR ADVANTAGES OF THE INVENTION

In describing a fragrance sack in accordance with the preferred embodiment of the invention those skilled in the art will recognize several advantages which singularly distinguish the subject invention from the heretofore known prior art.

A particular advantage of the subject invention is the provision of a replaceable scenting element located in a pocket section of the fragrance sack. In this connection, fragrance sacks described in the prior art were generally of a permanent nature wherein the fragrance could not be changed, or in many cases, even renewed. Accordingly, when the fragrance wore out or became unappealing to the user, the fragrance sack was frequently discarded. In sharp contrast, the present invention provides the user to not only renew the scented element with the same fragrance at any time, but also to change fragrances by the mere replacement of a scenting element.

Another specific advantage of the subject invention is the provision of an attractive anchoring means and receiving pockets secure the scented element to the fragrance sack. Unlike prior sacks having replaceable cartridges, the present invention minimizes loss or damage of the scenting element due to handling of the fragrance sack. Moreover, the receiving pocket provides an insulating layer between the scenting element and the outer surface of the fragrance sack so that over saturation of the scenting element does not result in the staining of the sack surface.

In describing the invention, reference has been made to a preferred embodiment. Those skilled in the art, however, and familiar with the disclosure of the subject invention, may recognize additions, deletions, substitutions, modifications and/or other changes which will fall within the purview of the invention as defined in the following claims.

What is claimed is:

1. A fragrance holder for selectively scenting the surrounding area and items in the surrounding area by permeation of scents into the air and nearby materials comprising:

a soft, compressibly flexible porous sack having an outer surface and a periphery defining an enclosed, bounded area, and a portion of said sack periphery forming indenting pocket extending inwardly from said periphery and defining an opening in said periphery;

a stuffing material within said sack and about said pocket;

a unitary rechargeable scenting element;

an elongated flexible ribbon connector means having a first end releasably secured to said outer surface and a second end secured to said scenting element, said ribbon having a length sufficient to insert said scenting element into said pocket and also to operatively retrieve said scenting element from said pocket for presence outside thereof while remaining connected to a portion of said sack via said connector means;

said ribbon connector means and said scenting element extending into said cavity opening through said opening whereby said scenting element is separated form said stuffing material by said pocket.

* * * * *